United States Patent [19]

De Thomas et al.

[11] 4,182,721

[45] Jan. 8, 1980

[54] CATALYTIC HYDROGENATION OF CARBONYL CONTAINING ORGANIC COMPOUNDS

[75] Inventors: Waldo R. De Thomas, Parsippany; Eugene V. Hort, Wayne, both of N.J.

[73] Assignee: GAF Corporation, New York, N.Y.

[21] Appl. No.: 938,008

[22] Filed: Aug. 30, 1978

[51] Int. Cl.² ............................................ C07D 307/44
[52] U.S. Cl. .................................. 260/347.8; 252/438; 252/469; 252/470; 252/477 Q; 260/690; 568/881
[58] Field of Search ............................ 260/347.8, 690; 568/881; 252/470

[56] References Cited

U.S. PATENT DOCUMENTS

| | | | |
|---|---|---|---|
| 2,071,704 | 2/1937 | Normann et al. | 260/347.8 |
| 2,763,666 | 9/1956 | Mastagli | 260/347.8 |
| 2,948,687 | 8/1960 | Hadley | 252/470 |
| 3,880,940 | 4/1975 | Baer et al. | 568/881 |
| 3,997,478 | 12/1976 | Petro | 252/470 |

*Primary Examiner*—Richard Raymond
*Attorney, Agent, or Firm*—Walter Kehm; Walter Katz

[57] ABSTRACT

This invention relates to catalytic hydrogenation of organic compounds containing carbonyl groups, and, particularly, to the effective and rapid reduction of the carbonyl group to the corresponding hydroxy group, sometimes even very selectively in the presence of a carbon-to-carbon unsaturated group in the same compound, using as a hydrogenation catalyst Raney nickel having molybdenum adsorbed thereon.

9 Claims, No Drawings

CATALYTIC HYDROGENATION OF CARBONYL CONTAINING ORGANIC COMPOUNDS

BACKGROUND OF THE INVENTION

1. Field of the Invention

This invention relates to catalytic hydrogenation of organic compounds containing carbonyl groups, and, more particularly, to the effective and rapid reduction of the carbonyl group to the corresponding hydroxy group, sometimes even very selectively in the presence of a carbon-to-carbon unsaturated group in the same compound.

2. Description of the Prior Art

Many hydrogenation catalysts are known in the art for the reduction of carbonyl functional groups in organic compounds. Several are available, too, for selectively reducing the carbonyl group to the corresponding hydroxy group in the presence of a carbon-to-carbon unsaturated group in the same compound. Such catalysts are described in detail, for example, in *Catalytic Hydrogenation* by R. L. Augustine M. Dekker Inc., N. Y. (1965). As disclosed in this book, a copper-chromium oxide ("copper chromite") catalyst will promote the hydrogenation of an aldehyde group in preference to a generally more reactive vinyl group. However, such selective hydrogenations generally require extreme pressure (3000 psi) and high temperature (140°–160° C.) conditions. A related catalyst, zinc-chromium oxide, makes use of the ability of zinc ions to inhibit the hydrogenation of double bonds for conversion of unsaturated esters to unsaturated alcohols, but also necessitates high pressures and temperatures.

Conventional Raney nickel catalysts, which have been used for some time as hydrogenation catalysts, also are not entirely satisfactory for reduction of carbonyl groups, because of their relative inactivity.

Accordingly, it is an object of the present invention to provide an improved method for reducing carbonyl groups in organic compounds, and, particularly to a method for selectively hydrogenating carbonyl groups, sometimes even in the presence of carbon-to-carbon unsaturated groups. A specific object herein is to provide such a method which can be carried out effectively and rapidly at low pressures and temperatures, in an economical process, using an inexpensive catalyst, whereby the desired product is obtained in high yield with a minimum of by-products.

SUMMARY OF THE INVENTION

These and other objects and features of the invention are accomplished herein by forming a reaction mixture of the carbonyl-containing organic compound with a catalyst consisting essentially of Raney nickel having a molybdenum compound adsorbed thereon, and introducing hydrogen into the mixture to reduce the carbonyl group to the corresponding hydroxy group. In a specific embodiment of the invention, the carbonyl group is reduced selectively in the presence of a carbon-to-carbon unsaturated group.

DESCRIPTION OF THE PREFERRED EMBODIMENTS

In general, the hydrogenation reaction is run with about 0.2–30% by weight of the catalyst based on the weight of the organic compound, either in a solvent-free medium, or in a suitable solvent, at a temperature ranging from about room temperature to about 120° C., and at a pressure ranging from about atmospheric to about 1000 psig. Of course, the reaction conditions will vary depending upon the nature of the compound to be hydrogenated.

The catalyst used in the process of the present invention is prepared from Raney nickel solids which are suspended in a liquid medium, preferably in water. Then suitable amounts of a molybdenum compound is added to the suspension and the mixture is stirred so that the molybdenum compound can be adsorbed onto the Raney nickel solids. Generally, the improved Raney nickel catalyst herein is prepared starting with commercially available Raney nickel, which is usually a suspension of about 50% by weight of nickel in water. The commercial slurry may be diluted, if desired, to provide a stirrable concentration of the Raney nickel for reaction with the molybdenum compound. The suitable amount of the molybdenum compound is added as a solid, dispersion or a solution thereof to the Raney nickel suspension. Typical molybdenum compounds include various molybdenum salts and oxides, including ammonium and alkali molybdates, molybdic trioxide, and the like. Preferably the molybdenum compound is at least partially soluble in the liquid medium of the nickel suspension. The mixture is then stirred at room temperature for a period of time which is sufficient to adsorb most of the molybdenum compound onto the Raney nickel solids. Usually about 1 minute to 24 hours is suitable for this purpose, and about one hour generally is ample to adsorb the desired amount of the molybdenum compound onto the nickel solids. The resulting aqueous suspension may then be used as such as catalyst for a hydrogenation process. Any excess molybdenum compound present in suspension or solution does not interfere with the hydrogenation process, and, therefore, filtering of the catalyst suspension is unnecessary.

Suitably about 0.1–15 parts by weight of adsorbed molybdenum per 100 parts by weight of Raney nickel solids present is used as the catalyst composition. In practice, the amount of molybdenum in the catalyst may be determined, after additions of known amounts of the molybdenum compound, by analysis of residual molybdenum still in solution after stirring for given periods of time. Alternatively, the catalyst itself may be analyzed for nickel and molybdenum content.

Optionally, one or more additional metals, such as copper, cobalt, tungsten, zirconium, platinum or palladium, may be included in the catalyst, as metal adsorbed on the Raney nickel solids or as metal originally present in the Raney nickel alloy.

The results with the catalyst used herein are very favorable and effective compared to those obtained with untreated Raney nickel or with Raney nickel alloy catalysts containing molybdenum which was present in the Raney alloy before leaching.

A feature of the process of the invention is its ability to effectively reduce carbonyl groups in organic compounds, sometimes even selectively in the presence of carbon-to-carbon unsaturated groups. For example, furfural is reduced substantially to furfuryl alcohol in the process of the invention. In contrast, a similar process, using Raney nickel itself, or Raney nickel prepared from a molybdenum-containing alloy, does not hydrogenate carbonyl groups as efficiently, and forms considerable amounts of tetrahydrofurfuryl alcohol by-product during the reduction of furfural.

The invention now will be illustrated with reference to the following specific examples, which are to be considered as illustrative, but not limiting of, the invention herein.

EXAMPLE 1

Adsorption of Molybdenum on Raney Nickel

To 10.0 g aliquots of Raney nickel solids in 40 ml of water were added various proportions of molybdenum in the form of ammonium molybdate. The suspensions were stirred at room temperature and, at intervals, filtered and the filtrates analyzed for molybdenum content. The following Table I gives the extent of adsorption of molybdenum as a function of time of stirring.

TABLE I

| Time | Ratio of Wt. of Mo to Wt. of Raney Ni Solids | | | | |
|---|---|---|---|---|---|
| | 0.03 | 0.04 | 0.06 | 0.08 | 0.12 |
| | % of Mo Charge Adsorbed on Catalyst | | | | |
| 10 min. | 86 | 83 | 78 | 75 | 73 |
| 1 hr. | 92 | 87 | 82 | 79 | 75 |
| 24 hrs. | 96 | 93 | 89 | 88 | 87 |

EXAMPLE 2

To 20.0 g. of commercial Raney nickel containing about 50% nickel particles as an aqueous slurry was added solid ammonium molybdate, $(NH_4)_6Mo_7O_{24}\cdot 4H_2O$, and the mixture was stirred for an hour. The catalyst thus prepared then was used directly in the hydrogenation process. Catalysts were prepared in this manner corresponding to between 0.1–15 parts by weight of molybdenum added per 100 parts of Raney nickel solids.

EXAMPLE 3

Hydrogenation of Formaldehyde

Two identical hydrogenations were run using (A) unmodified Raney nickel and (B) Raney nickel containing about 4 parts of molybdenum adsorbed per 100 parts of Raney nickel solids. In each hydrogenation 7.25 g. of formaldehyde in 493 ml. of water was catalyzed with 10.0 g. of the catalyst. After hydrogenation at 60° C. and 3000 psig for 6 hours, the following results were obtained.

TABLE II

| | Carbonyl No. | % Formaldehyde |
|---|---|---|
| Initial Feed Solution | 27.1 | 1.45 |
| Catalyst of Hydrogenation | | |
| Unmodified Raney nickel (A) | 7.0 | 0.36 |
| Molybdenum adsorbed on Raney nickel (B) | 0.5 | 0.01 |

The results demonstrate that the process using the absorbed molybdenum on Raney nickel produced a more effective reduction of the formaldehyde than the unmodified Raney nickel catalyst.

EXAMPLE 4

Hydrogenation of Furfural

Three identical hydrogenations were run using (A) unmodified Raney nickel (B) Raney nickel containing 3% molybdenum alloyed as in the prior art, and (C) Raney nickel containing about 4 parts by weight molybdenum adsorbed per 100 parts of Raney nickel solids according to this invention.

In each hydrogenation, 175 g of furfural in 325 g. aqueous isopropyl alcohol was catalyzed with 10.0 g of the catalyst. After hydrogenation at 60° C. and 300 psg for 6 hours, the following results were obtained.

TABLE III

| | Catalyst Used | | |
|---|---|---|---|
| | (A) | (B) | (C) |
| Components of Reaction Product | % of Component | | |
| Furfuryl Alcohol | 31.0 | 70.0 | 98.0 |
| Tetrahydrofurfuryl Alcohol | 51.9 | 25.8 | 1.6 |
| Tetrahydrofurfural | 7.4 | 0.9 | 0.0 |
| Fufural | 8.6 | 2.2 | 0.1 |
| Others | 1.1 | 1.1 | 0.3 |

The results in this process demonstrate the selectivity of the method herein for reduction of carbonyl groups effectively in the presence of a carbon-to-carbon unsaturated group.

What we claim is:

1. A method of effectively and rapidly reducing a carbonyl group present in an aldehyde organic compound which comprises:
    (a) forming a mixture of said compound and a Raney nickel catalyst comprising Raney nickel solids having adsorbed thereon a molybdenum compound in an amount of about 0.1–15 parts by weight molybdenum per 100 parts of the Raney nickel solids, and,
    (b) introducing hydrogen into said mixture thereby to reduce the carbonyl group of said compound to the corresponding hydroxy group.

2. A process according to claim 1 wherein said compound is formaldehyde.

3. A process according to claim 1 wherein said compound is furfural.

4. A process according to claim 1 in which said catalyst includes at least one additional metal selected from the group consisting of copper, cobalt, tungsten, zirconium, platinum and palladium.

5. A process according to claim 1 in which said catalyst is present in an amount of about 0.2–30% by weight of said compound.

6. A process according to claim 1 in which said compound is present in a solvent.

7. A process according to claim 1 wherein said reaction is run at a temperature range from about room temperature to about 120° C.

8. A process according to claim 1 wherein said reaction is run at a pressure range from about atmospheric to 1000 psig.

9. A process according to claim 1 wherein said carbonyl group is selectively reduced to the corresponding hydroxy group in the presence of a carbon-to-carbon unsaturated group in said compound.

* * * * *